United States Patent [19]

Kohnke

[11] Patent Number: 5,127,397
[45] Date of Patent: Jul. 7, 1992

[54] PROTECTIVE DEVICE KIT FOR USE IN PULMONARY VENTILATION TREATMENT BY THE MOUTH-TO-MOUTH OR MOUTH-TO-NOSE METHODS

[75] Inventor: Ole B. Køhnke, Lyngby, Denmark

[73] Assignee: Ambu International A/S, Glostrup, Denmark

[21] Appl. No.: 575,620

[22] Filed: Aug. 31, 1990

[30] Foreign Application Priority Data

Sep. 4, 1989 [DK] Denmark ................. 4367

[51] Int. Cl.⁵ .................................. A61M 16/00
[52] U.S. Cl. ..................... 128/202.28; 128/203.11
[58] Field of Search ............. 128/202.28, 202.29, 128/203.11

[56] References Cited

U.S. PATENT DOCUMENTS

| | | | |
|---|---|---|---|
| 3,286,710 | 11/1966 | Bartlett | 128/203.11 |
| 3,626,936 | 12/1971 | Barker | 128/203.11 |
| 3,809,079 | 5/1974 | Buttaravoli | 128/206.24 |
| 4,050,457 | 9/1977 | Davidson | 128/202.28 |
| 4,510,931 | 4/1985 | Henderson et al. | 128/202.28 |
| 4,711,237 | 12/1987 | Kaiser | 128/202.28 |
| 4,819,628 | 4/1989 | Eisenberg et al. | 128/203.11 |
| 4,858,605 | 8/1989 | Levy | 128/203.11 |
| 4,867,148 | 9/1989 | Gomez | 128/202.28 |
| 4,909,245 | 3/1990 | Wollenhaupt | 128/203.11 |

FOREIGN PATENT DOCUMENTS

| | | |
|---|---|---|
| 3381278 | 11/1980 | Australia . |
| 0081943 | 6/1983 | European Pat. Off. . |
| 2520422 | 11/1975 | Fed. Rep. of Germany . |
| 2742213 | 3/1979 | Fed. Rep. of Germany ............ 128/203.11 |

OTHER PUBLICATIONS

"KMS 1ST Responder Mask", Keller Medical Specialties Armstrong Industries, Inc.
Laerdal Pocket Mask, Armstrong Industries, Inc.

Primary Examiner—Edgar S. Burr
Assistant Examiner—Aaron J. Lewis
Attorney, Agent, or Firm—Watson, Cole, Grindle & Watson

[57] ABSTRACT

A protective device kit for use in pulmonary ventilation treatment including a film mask for positioning over a patient's mouth and nose regions and a one-way valve mounted centrally in the film mask and comprising a valve housing having a valve seat provided with inlet openings and having an internally situated valve flap which, in the closed position of the valve, covers the inlet openings of the valve seat, and one or more outlet openings provided in the side wall of the valve housing, and further including a flat box for encasing closely and protecting the film mask in its folded state.

8 Claims, 4 Drawing Sheets

PROTECTIVE DEVICE KIT FOR USE IN PULMONARY VENTILATION TREATMENT BY THE MOUTH-TO-MOUTH OR MOUTH-TO-NOSE METHODS

BACKGROUND OF THE INVENTION

The present invention relates to a protective device kit for use in pulmonary ventilation treatment by the mouth-to-mouth or the mouth-to-nose methods, which device comprises a face mask consisting of a thin flexible film to be positioned over the mouth and nose regions of a patient, and a one-way valve positioned in a centrally located opening in the film mask and so constructed that it permits the user of the protective device to blow air into the patient's respiratory passages and prevents exhalation air from the patient's respiratory passages from flowing into the mouth of the user.

While earlier pulmonary ventilation by the mouth-to-mouth or the mouth-to-nose methods in emergency situations was largely carried out without remedies, i.e. the person to administer the pulmonary ventilation put his mouth in direct contact with the patient's mouth or nose, the wide-spread fear of catching serious diseases by oral contact with a stranger has created a need to protect the persons who carry out the pulmonary ventilation in the manner just described against the transmission of infectious matter from a patient, especially from his blood and saliva, including also inhalation of airborne matter which is exhaled through the patient's mouth and/or nose in connection with the air ventilation.

A protective device of the kind described above is disclosed in U.S. Pat. No. 3,802,428 which discloses a mask in the form of an oval flexible piece of film having a strap fixed at its opposed ends to be placed around the back of the rescuer's neck. The one-way valve of the known protective device is composed of a tubular body which may be made from the same material as the face mask. At its one end the tubular body is hermetically secured to the edge of the central opening in the face mask and the other end is intended for insertion into the mouth of the patient during the pulmonary ventilation. The known protective device may be folded to form a flat packet, but it is not suitable for use in mouth-to-nose pulmonary ventilation and furthermore it will be a nuisance to the rescuer when he has to carry out cardiac massage, too.

Another prior art device is disclosed in EP patent publication No. 0,303,367 A2. This known protective device comprises a substantially rectangular flexible protective sheet provided with a centrally positioned opening, the edge of which is connected to the edge of a rigid tube for insertion into the patient's mouth and to an internal collapsible one-way valve.

Also, the latter prior art protective means is associated with the drawback that it can be used only for mouth-to-mouth pulmonary ventilation. Owing to the presence of the rigid tube it cannot be folded up compactly, either, to a small volume.

Typically, the need for carrying out pulmonary ventilation by the mouth-to-mouth or the mouth-to-nose methods arises in case of, e.g., sudden heart failure, traffic or drowning accidents where the persons present who are capable of carrying out pulmonary ventilation and optionally cardiac massage are unprepared for performing first-aid. Therefore they do not normally carry any protective means and consequently the patient may not immediately receive the vital resuscitation treatment due to the rescuer's fear of transmission of infectious matter. It would be desirable to provide everybody who might wish to be able to carry out immediate and vital pulmonary ventilation with protective means of the construction described above and so designed that the training methods used so far when practising mouth-to-mouth and mouth-to-nose ventilation and cardiac massage may still be carried out as taught when the protective means is taken into use. However, the solutions suggested so far have not proved fully satisfactory, the known protective means being so bulky that the users are very unlikely to carry it along in all situations and in particular when very lightly clad, e.g., on the beach, or because such means cannot be used for both mouth-to-mouth and mouth-to-nose pulmonary ventilation.

It is the object of the present invention to provide a protective device of the kind described above and of small enough dimensions for it to be kept in a box which also serves to provide adequate protection of the protective device for it to be kept safely therein for long periods of time and which is so small that it may conveniently be carried along as any other personal belonging normally carried along irrespective of one's whereabouts and which is also suitable for use in both the mouth-to-mouth and the mouth-to-nose methods.

SUMMARY OF THE INVENTION

This object is obtained with the protective device kit according to the invention described initially which is characterized in that the one-way valve comprises a flat valve housing having a valve seat provided with inlet openings, an internally located valve flap which, in the closed position of the valve, covers the inlet openings of the valve seat, and one or more outlet openings provided in the side wall of the valve housing, and that the protective device kit further comprises a flat box for encasing closely and protecting the film mask in its folded state, which box being provided with suspension means.

The one-way valve, which is a part of the protective device of this invention, is of a very compact construction which, however, is also functionally very reliable. If a circular valve housing and a circular valve flap are used it will be possible to reduce the dimensions of the valve so much that the dimensions of the box for encasing and protecting the protective device do not exceed 33×33 ×14 mm. This means that the protective device according to the invention can be held in, e.g., a key ring, without being a nuisance to the person carrying the key ring.

By permitting the protective device to be carried along in the manner described above the protective device may always be at hand and ready for use even when least expected incidents occur.

The noted valve is further suitable for use in both the mouth-to-mouth and the mouth-to-nose methods as no parts thereof are to be inserted into the patient's mouth or nose. The construction of the valve permits it to be of such a size that it fits readily into the mouth of the rescuer when it covers either the mouth or the nose region of the patient, and the positioning of the outlet opening in the side wall of the valve housing ensures that the administration of air is not blocked by close contacting the mask against the face of the patient.

The box is preferably a plastic box produced by injection moulding. The box is preferably provided with a closing means which ensures that the box may be closed so tightly that no dirt enters the box when carried along in a pocket or a bag. In the preferred embodiment the box is provided with an external eyelet permitting suspension from a key ring.

The film mask is preferably oblong and double-curved, i.e., curved in both longitudinal and cross sections, so that it appears convex as seen from the rescuer's side and concave from the patient's side when in the unfolded state and in use, thereby ensuring that a sufficient amount of film is available for bringing those parts of the mask which surround the patient's mouth and nose, respectively, into airtight contact with the patient's face without shutting off access to the nose and the mouth, respectively, when used. It is preferably wide enough to cover the patient's face from the root of his nose to the point of his chin.

The film is preferably a plastic film of a thickness of about 0.03 mm and may be made from, e.g., polyethylene or the like transparent, thermoplastic material.

The double-curved shape may conveniently be obtained by welding together two adjacent edges of a generally triangular piece of film to the corresponding adjacent edges of another generally triangular piece of film.

In use of a double-curved film mask the valve opening and the valve are preferably slightly displaced relative to the longitudinal central axis of the mask and when used such mask is positioned so that the valve is situated at the half of the mask which covers the chin. Thus a convenient location of the valve is obtained, viz. inclined before the nostrils, when the tip of the nose is positioned centrally in the cavity of the mask.

In a preferred embodiment the film mask is provided with securing means comprising an endless elastic string which forms a loop at each end of the film mask, which loops are intended to be positioned around the patient's ears. Those parts of the elastic string that extend along the longitudinal edges of the mask are preferably embedded in channels which are made by folding back and welding of said longitudinal edges to the film. The securing of the loops around the patient's ears in this manner is easily performed, since both the rescuer's hands are free as the patient's head is not to be lifted.

The noted securing loops ensure safe positioning of the film mask which is crucial when pulmonary ventilation alternates with cardiac massage.

If the film mask is not constantly maintained in its correct position, there is a risk that the pulmonary ventilation and cardiac massage cannot be carried out at the correct rate and at the correct intervals. In this connection it should be noted that preferably the intervals between cardiac massage operations should not exceed about 7 seconds and that two pulmonary ventilations are carried out during each interval.

The valve used is preferably provided with a circular valve flap and the circular valve flap is preferably provided with a central protrusion serving to secure the membrane relative to a valve seat which is also circular.

According to a particularly preferred embodiment, the protective device according to the invention comprises a slightly arched circular valve flap, the edge of which is maintained in close contact with the valve seat by a light pressure thereby providing a further safety measure to prevent air from passing through the film mask in the unintended direction.

DESCRIPTION OF THE PREFERRED EMBODIMENTS

Figure 1:
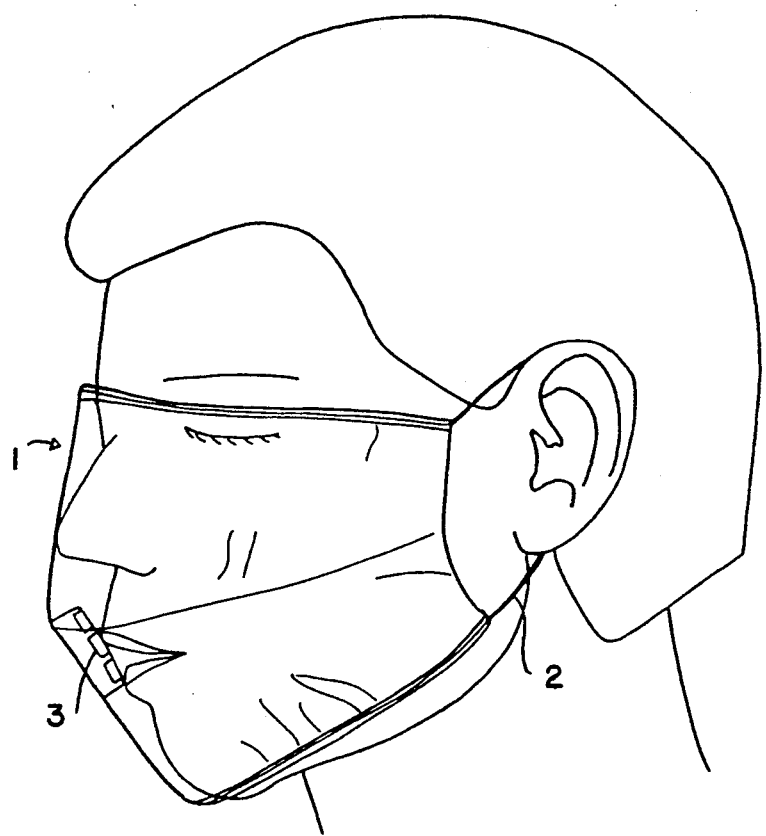
FIG. 1 is a side view of the head of a patient who wears a preferred embodiment of a film mask according to the invention.

FIG. 1 shows a film mask 1 which is maintained in an expanded state over the mouth and nose regions of a patient by means of an elastic string 2 positioned around the patient's ears, the mask covering his face from the root of his nose to his chin.

The film mask shown comprises a one-way valve 3 the construction of which will be subject to more detailed description below.

Figure 2:
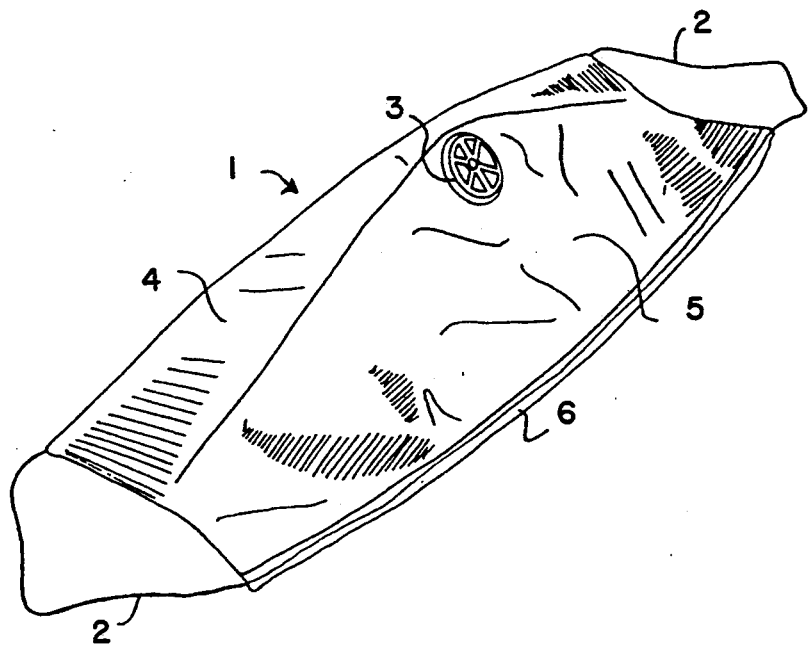
FIG. 2 is a perspective view of a double-curved film mask as illustrated in FIG. 1.

The shape of the film mask 1 shown in FIG. 1 is further illustrated in FIG. 2. As will appear from FIG. 2 the film mask 1 consists of a double-curved element comprising a left side 4 and a right side 5, and the valve 3 is positioned on the right side 5 and is slightly displaced relative to the central plane. The film mask 1 shown comprises at its two longitudinal edges channels 6 (only one shown in FIG. 2) which are formed by folding back the longitudinal edges and subsequent welding of the foldings onto the film mask. These channels 6 surround the elastic string 2 along the side edges of the film mask.

Figure 3:
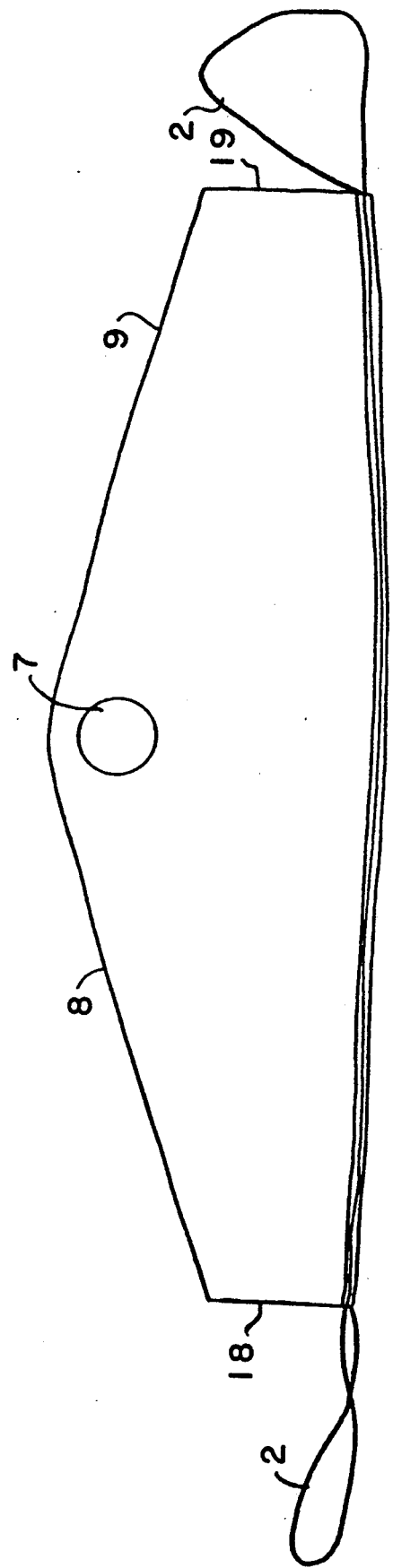
FIG. 3 shows a film mask (without valve) in its flat state and as seen from above.

This way of securing the string 2 to the face mask is also illustrated in FIG. 3 which additionally shows the location of an opening 7 into which the one-way valve 3 is to be mounted.

The production of a film mask as shown in FIG. 3 may be carried out by placing two pentagonal pieces of film as shown in FIG. 3 on top of each other and welding the two pieces of film together along the edges 8 and 9. If the opposite edges 18 and 19 are rather small or optionally zero the construction pieces of film assume a substantially or true triangular shape.

Figure 4:
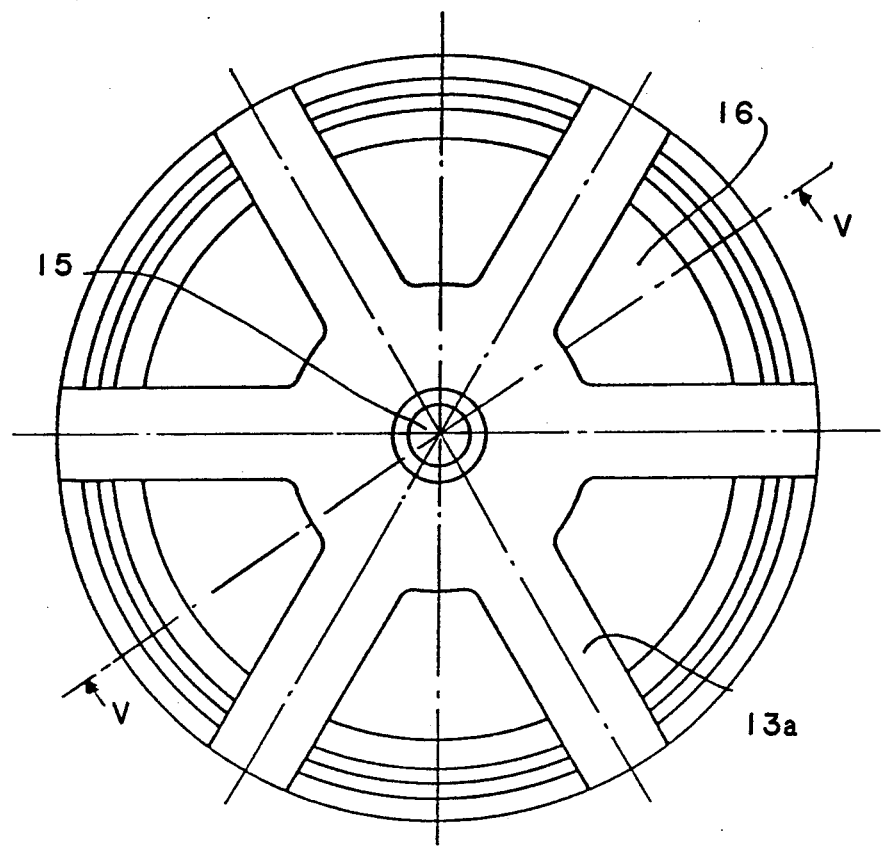
FIG. 4 shows a valve for use in a film mask according to the invention as seen from the front of the valve.
Figure 5:
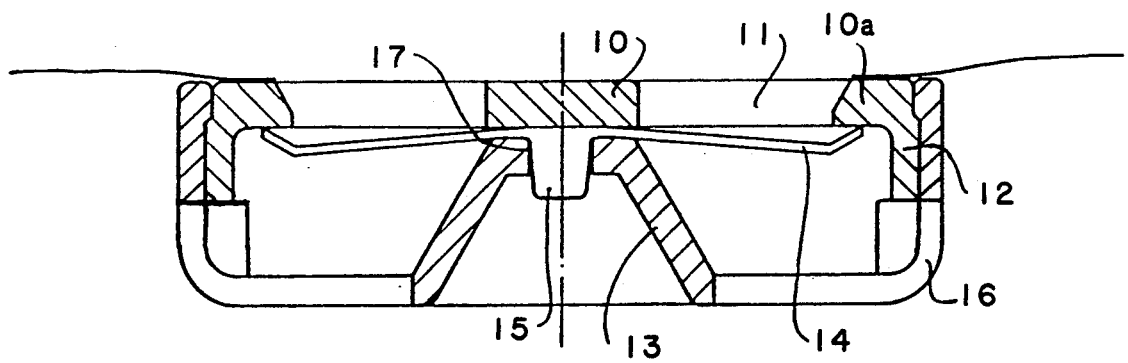
FIG. 5 is a sectional view along the line V—V in FIG. 4 of the valve according to FIG. 4.

The valve shown in FIGS. 4 and 5 includes a housing provided by a valve seat 10 and a cover cap 23, as well as a circular valve flap 24 positioned within the housing. The valve seat 10 defines an outer wall 10a of the housing having inlet openings 11 and an annular flange 12. The cover cap 13 defines an inner wall 13a of the housing and an annular wall which, together with the annular wall of the valve seat, defines a lateral side wall of the housing. The cover cap includes openings 16 to provide outlet openings along at least the lateral side wall of the housing. The cover cap also includes a central protrusion for centering and fixing the circular valve flap 14 which is constantly pressed against the valve seat 10.

Figure 7:
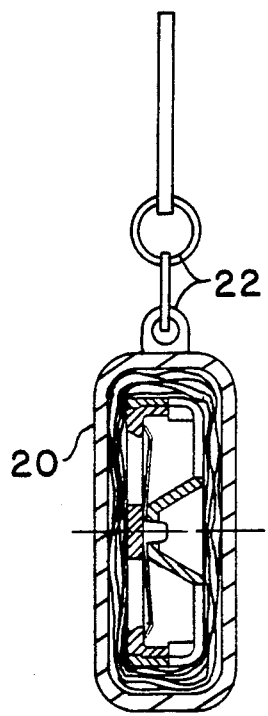
FIG. 7 shows the protective device kit according to FIG. 6 as seen from the end, wherein the box and its contents are shown in section.
Figure 6:
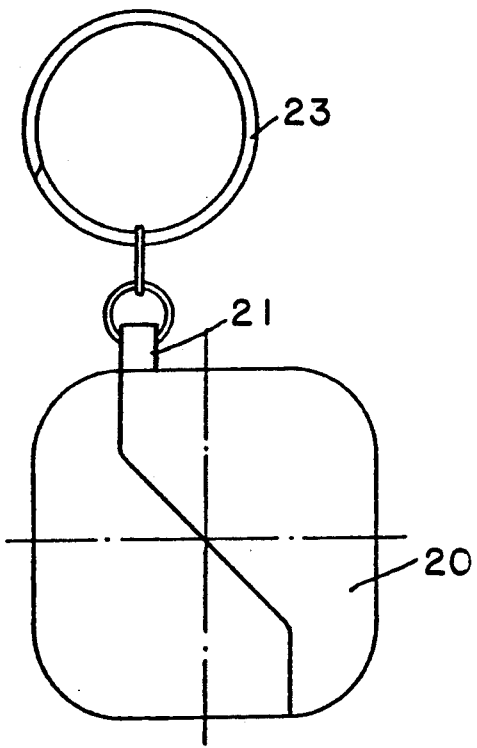
FIG. 6 is a side view of a protective device kit according to the invention when held in a key ring.

FIGS. 6 and 7 show a box 20 containing a protective device according to the invention in its folded state.

At its one end the box 20 is provided with an eyelet 21 through which two chain links 22 connect the box to a key ring 23.

I claim:

1. A protective device kit for use in pulmonary ventilation treatment of a patient, said kit comprising a face mask of a thin flexible film for positioning over a patient's mouth and nose regions, and a one-way valve provided in a centrally located opening in the film ask and constructed so that it permits the user of the protective device to blow air into the respiratory passages of the patient and prevents air from the patient's respiratory passages from flowing into the mouth of the user, said one-way valve is attached to said mask to cover said centrally located opening, said one-way valve comprising a flat valve housing which defines an outer wall, an inner wall and a lateral side wall, said outer wall including inlet openings, and at least said lateral side wall including at least one outlet opening; and a valve flap within said housing for closing said inlet openings when no air is being blow through said inlet openings, and said kit further comprising a flat box for encasing closely and protecting the film mask in its folded state, said box being provided with suspension means.

2. A protective device kit according to claim 1, wherein said face mask is oblong and double-curved.

3. A protective device kit according to claim 1, wherein said face mask comprises two generally triangular pieces of film whose adjacent edges are connected together.

4. A protective device kit according to claim 1, wherein said face mask includes securing means comprising elastic strings with loops to be positioned around the patient's ears.

5. A protective device kit according to claim 1, wherein said one-way valve comprises a circular valve flap having a central protrusion which is fixed relative to the valve seat provided with openings.

6. A protective device kit according to claim 5, wherein said valve flap is maintained in close contact with the valve seat in its resting position by a light pressure.

7. A protective device kit according to claim 1, wherein the position of the one-way valve is displaced towards the one side of the double-curved surface of the film mask relative to a longitudinal central plane of the mask.

8. A protective device kit according to claim 1, wherein said film mask is composed of a transparent material.

* * * * *